United States Patent
Heaton et al.

(10) Patent No.: US 9,289,326 B2
(45) Date of Patent: Mar. 22, 2016

(54) REDUCED-PRESSURE, WOUND-CLOSURE AND TREATMENT SYSTEMS AND METHODS

(75) Inventors: Keith Patrick Heaton, Poole (GB); Ian Hardman, Bournemouth (GB); Christopher Guy Coward, Wareham (GB); Collin John Hall, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 988 days.

(21) Appl. No.: 13/401,502

(22) Filed: Feb. 21, 2012

(65) Prior Publication Data

US 2012/0150133 A1 Jun. 14, 2012

Related U.S. Application Data

(62) Division of application No. 12/467,203, filed on May 15, 2009, now Pat. No. 8,142,419.

(60) Provisional application No. 61/109,410, filed on Oct. 29, 2008, provisional application No. 61/109,486, filed on Oct. 29, 2008, provisional application No. 61/109,390, filed on Oct. 29, 2008, provisional application No. 61/109,448, filed on Oct. 29, 2008.

(51) Int. Cl.
*A61F 13/00* (2006.01)
*A61B 17/00* (2006.01)
*A61M 1/00* (2006.01)

(52) U.S. Cl.
CPC ....... *A61F 13/00068* (2013.01); *A61B 17/0057* (2013.01); *A61F 13/00025* (2013.01);
(Continued)

(58) Field of Classification Search
CPC ................ A61B 17/0057; A61B 2017/00575; A61B 2017/00646; A61B 2017/00676; A61F 13/00025; A61F 13/00034; A61F 13/00068; A61F 13/00987; A61M 1/0088
USPC ........................................................... 604/540
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 8/1982
AU 745271 4/1999
(Continued)

OTHER PUBLICATIONS

International Search Report for corresponding PCT application PCT/US2009/044264 mailed May 11, 2009.
(Continued)

*Primary Examiner* — Philip R Wiest
*Assistant Examiner* — Benjamin Klein

(57) ABSTRACT

A reduced-pressure, wound closure system is presented that generates a closing force on a surface wound and optionally provides reduced pressure to a body cavity or tissue site. The sealed contracting member, when placed under reduced pressure, generates the closing force. One illustrative system includes a first attachment member and a second attachment member, a sealed contracting member coupled to the first attachment member and the second attachment member, and wherein the closing force is generated between the first attachment member and the second attachment member when reduced pressure is supplied to the sealed contracting member. Other systems and methods are presented.

16 Claims, 4 Drawing Sheets

(52) U.S. Cl.
CPC ..... *A61F13/00034* (2013.01); *A61F 13/00987* (2013.01); *A61M 1/0088* (2013.01); *A61B 2017/00575* (2013.01); *A61B 2017/00646* (2013.01); *A61B 2017/00676* (2013.01); *A61F 13/00029* (2013.01); *A61F 13/00038* (2013.01); *A61M 1/0092* (2014.02); *Y10T 29/49* (2015.01); *Y10T 29/49826* (2015.01); *Y10T 156/1052* (2015.01); *Y10T 156/1056* (2015.01); *Y10T 156/1057* (2015.01); *Y10T 156/1062* (2015.01); *Y10T 156/1304* (2015.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,795,435 A | 1/1989 | Steer |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A * | 6/2000 | Zamierowski ............... 604/289 |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2001/0029956 A1 | 10/2001 | Argenta et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0030304 A1 | 2/2004 | Hunt et al. |
| 2005/0085795 A1 | 4/2005 | Lockwood et al. |
| 2006/0079852 A1 | 4/2006 | Bubb et al. |
| 2008/0103489 A1 | 5/2008 | Dahners |
| 2009/0287181 A1 * | 11/2009 | Kagan ............... 604/506 |

FOREIGN PATENT DOCUMENTS

| | | |
|---|---|---|
| AU | 455496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | WO01/85248 A | 11/2001 |

(56) References Cited

FOREIGN PATENT DOCUMENTS

| WO | WO2005082435 | A1 | 9/2005 |
|---|---|---|---|
| WO | WO2006056294 | A1 | 6/2006 |
| WO | WO2006116281 | A2 | 11/2006 |
| WO | WO2007/041642 | A | 4/2007 |
| WO | WO2008/064502 | A1 | 6/2008 |

OTHER PUBLICATIONS

N.A. Bagautdinov, "Variant of External Vacuum Aspiration in the Treatment of Purulent Diseases of the Soft Tissues," Current Problems in Modem Clinical Surgery: Interdepartmental Collection, edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for Pot International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

* cited by examiner

REDUCED-PRESSURE, WOUND-CLOSURE AND TREATMENT SYSTEMS AND METHODS

RELATED APPLICATIONS

The present invention is a divisional of U.S. patent application Ser. No. 12/467,203, entitled "Reduced-Pressure, Wound-Closure and Treatment Systems and Methods," filed on May 15, 2009 now U.S. Pat. No. 8,142,419, which claims the benefit, under 35 USC §119(e), of the filing of U.S. Provisional Patent Application Ser. No. 61/109,410, entitled "Reduced-Pressure, Wound-Closure System and Method," filed Oct. 29, 2008; U.S. Provisional Patent Application Ser. No. 61/109,486, entitled "Reduced-Pressure, Abdominal Treatment System and Method," filed Oct. 29, 2008; U.S. Provisional Patent Application Ser. No. 61/109,390, entitled "Open-Cavity, Reduced-Pressure Wound Dressing and System," filed Oct. 29, 2008; and U.S. Provisional Patent Application Ser. No. 61/109,448, entitled "Reduced-Pressure, Deep-Tissue Closure System and Method," filed Oct. 29, 2008. All of these applications are incorporated herein by reference for all purposes.

BACKGROUND

The present invention relates generally to medical treatment systems and, more particularly, to reduced-pressure, wound-closure and treatment systems and methods.

Whether the etiology of a wound, or damaged area of tissue, is trauma, surgery, or another cause, proper care of the wound is important to the outcome. Unique challenges exist when the wound involves locations that require reentry, such as the peritoneal cavity and more generally the abdominal cavity. Many times when surgery or trauma involves the abdominal cavity, establishing a wound management system that facilitates reentry allows for better and easier care and helps to address such things as peritonitis, abdominal compartment syndrome (ACS), and infections that might inhibit final healing of the wound and the internal organs. In providing such care, it may be desirable to remove unwanted fluids from the cavity, help approximate the fascia and other tissues, or finally to help provide a closing force on the wound itself at the level of the epidermis. Unless otherwise indicated, as used herein, "or" does not require mutual exclusivity.

Currently, an abdominal opening on the epidermis may be closed using sutures, staples, clips, and other mechanical devices to allow the skin to be held and pulled. Such devices often cause puncture wounds or can cause other wounds. If severe edema occurs, tremendous pressure may be placed on the closure device and the pressure may cause harm. For example, if the pressure rises due to edema, the sutures may tear out.

With respect to an overall system for allowing reentry into the abdominal cavity, a number of techniques have been developed. One approach is to place towels into the cavity and then use clips, such as hemostats, to close the skin over the towels. While simple and fast, the results are regarded as suboptimal. Another approach is the so-called "Bogota bag." With this approach, a bag is sutured into place to cover the open abdomen in order to provide a barrier. Still another approach, sometimes called a "vac pack," is to pack towels in the wound and then place a drain into the abdomen and cover the abdomen with a drape. Finally, a reduced pressure approach has been used. Such an approach is shown in U.S. Pat. No. 7,381,859 to Hunt et al. and assigned to KCI Licensing, Inc. of San Antonio, Tex. U.S. Pat. No. 7,381,859 is incorporated herein by reference for all purposes.

SUMMARY

Problems with existing wound closure devices and reduced-pressure treatment systems are addressed by the systems, apparatus, and methods of the illustrative embodiments described herein. According to one illustrative embodiment, a reduced-pressure, wound-closure system for providing a closing force to a surface wound on a patient includes a first attachment member for releasably attaching to a first portion of the patient's epidermis proximate an edge of the surface wound and a second attachment member for releasably attaching to a second portion of the patient's epidermis proximate the edge of the surface wound. The first attachment member is spaced from the second attachment member. The reduced-pressure, wound-closure system further includes a sealed contracting member coupled to the first attachment member and the second attachment member and operable to contract when placed under reduced pressure. The reduced-pressure, wound-closure system is operable to develop a closing force between the first attachment member and the second attachment member when reduced pressure is supplied to the sealed contracting member.

According to another illustrative embodiment, a reduced-pressure, wound-closure system for providing a closing force to a surface wound on a patient includes a first attachment member for releasably attaching to a first portion of the patient's epidermis proximate an edge of the surface wound and a second attachment member for releasably attaching to a second portion of the patient's epidermis proximate the edge of the surface wound. The first attachment member is spaced from the second attachment member. The reduced-pressure, wound-closure system further includes a circumferential wall that is coupled to the first attachment member and the second attachment member. The reduced-pressure, wound-closure system further includes a sealed contracting member coupled to at least a portion of the circumferential wall and operable to contract when placed under reduced pressure. A reduced-pressure source is fluidly coupled to the sealed contracting member and is operable to deliver a reduced pressure to the sealed contracting member. A closing force is developed when reduced pressure is supplied by the reduced-pressure source to the sealed contracting member.

According to another illustrative embodiment, a reduced-pressure, wound-closure and treatment system for providing a closing force to a surface wound on a patient and for delivering reduced pressure to tissue site includes a wound-closing subsystem and a reduced-pressure treatment subsystem.

According to another illustrative embodiment, a method of manufacturing a reduced-pressure, wound-closure system for providing a closing force to a surface wound on a patient includes the steps of: forming a first attachment member for releasably attaching to a first portion of the patient's epidermis proximate an edge of the surface wound and forming a second attachment member for releasably attaching to a second portion of the patient's epidermis proximate the edge of the surface wound. The method of manufacturing a reduced-pressure, wound-closure system further includes forming a sealed contracting member operable to contract when placed under reduced pressure and coupling the sealed contracting member to the first attachment member and the second attachment member.

According to another illustrative embodiment, a method for providing a closing force to a surface wound on a patient includes the steps of releasably attaching a first attachment member to a first portion of the patient's epidermis proximate an edge of the surface, wound and releasably attaching a second attachment member to a second portion of the patient's epidermis proximate the edge of the surface wound. The first attachment member is spaced from the second attachment member. The method of providing a closing force further includes providing a sealed contracting member and fluidly coupling the sealed contracting member to the first attachment member and the second attachment member. The sealed contracting member is operable to contract when placed under reduced pressure. The method of providing a closing force further includes supplying a reduced pressure to the sealed contracting member, whereby a closing force is developed between the first attachment member and the second attachment member.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
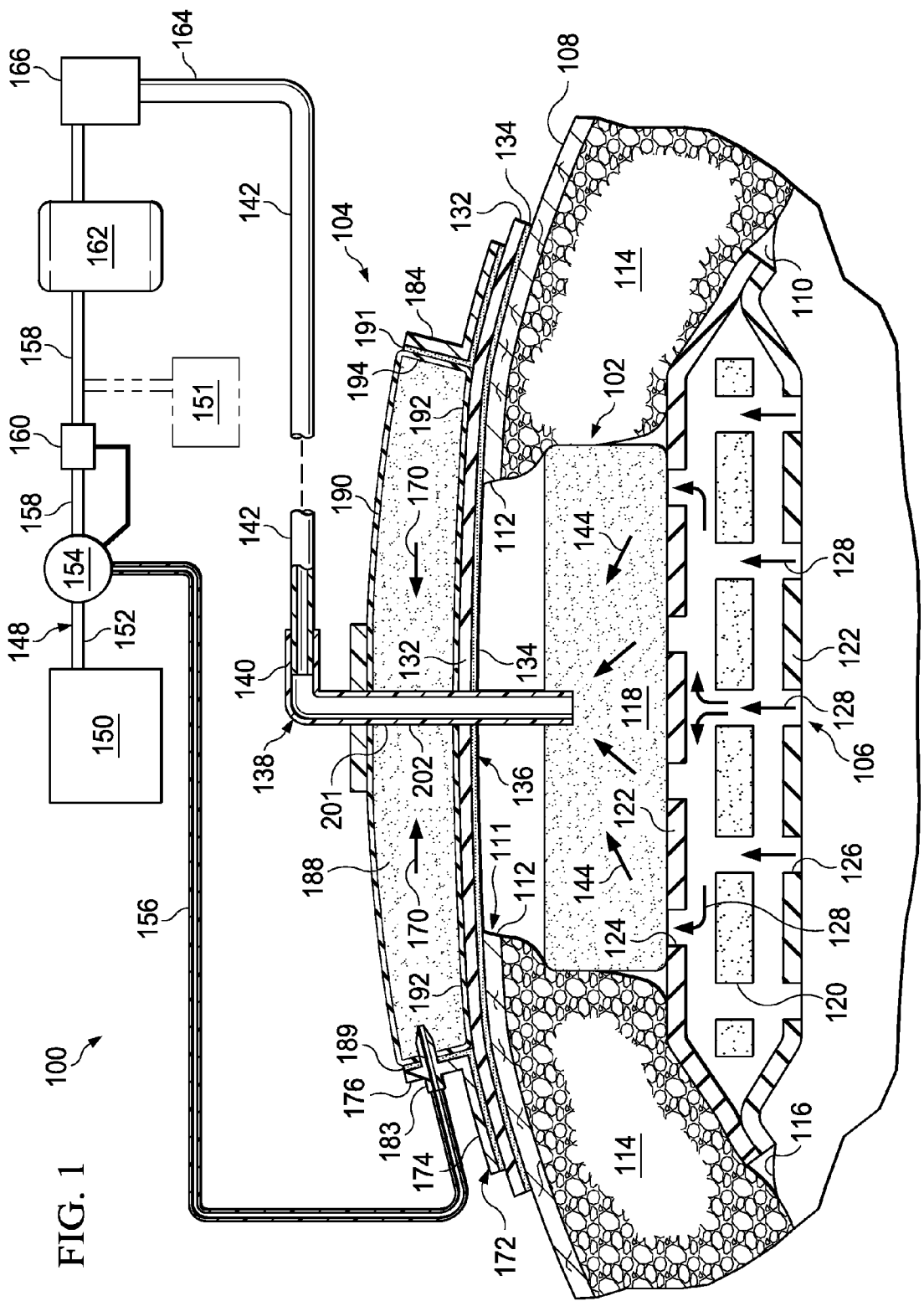
FIG. 1 is a schematic cross-section, with a portion presented as a block diagram, of an illustrative embodiment of a reduced-pressure, wound-closure and treatment system.
Figure 2:
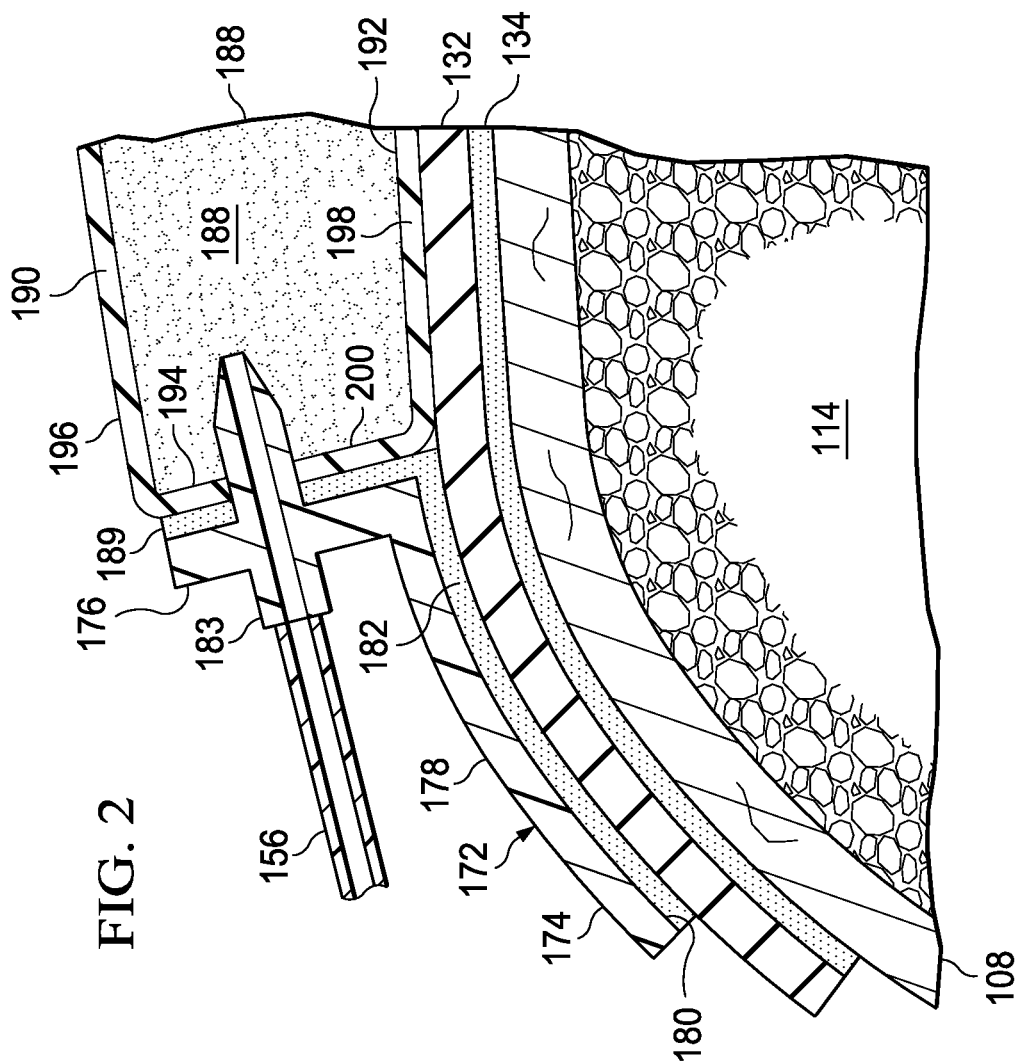
FIG. 2 is a schematic, cross-sectional view of a portion of the reduced-pressure, wound closure and treatment system of FIG. 1.

Referring to FIGS. 1-2, and initially to FIG. 1, an illustrative embodiment of a reduced-pressure, wound-closure and treatment system 100 is presented. The reduced-pressure, wound-closure and treatment system 100 may include a reduced-pressure treatment subsystem 102 and a wound-closure subsystem 104. The reduced-pressure treatment subsystem 102 may be used for treating a tissue site 106 with reduced pressure. The tissue site 106 may be the bodily tissue of any human, animal, or other organism, including bone tissue, adipose tissue, muscle tissue, dermal tissue, vascular tissue, connective tissue, cartilage, tendons, ligaments, or any other tissue. The tissue site 106 may be within a body cavity, such as an abdominal cavity 110, and may include various tissue layers including a wound in epidermis 108. Treatment with the reduced-pressure treatment subsystem 102 may include removing fluids, such as ascites or exudates, delivering reduced pressure, or providing a protective barrier.

In the illustrative embodiment, the reduced-pressure, wound-closure and treatment system 100 is presented in the context of the abdominal cavity 110 and a surface wound 111, which has wound edges 112. Other subdermal tissue 114 may also have been opened, such as fat tissue, muscles, fascia, etc. The abdominal cavity 110 is shown with abdominal contents 116, which form a surface or support.

The reduced-pressure treatment subsystem 102 of the reduced-pressure, wound-closure and treatment system 100 helps to deliver reduced pressure to the tissue site 106 and the abdominal cavity 110. The reduced-pressure treatment subsystem 102 includes a manifold 118 disposed within the abdominal cavity 110 to distribute reduced pressure within the abdominal cavity 110 and to receive fluids. The manifold 118 may include or be associated with a manifold member 120, or second manifold, in a non-adherent envelope 122. The non-adherent envelope 122 has apertures 124 on a first side and apertures 126 on a second, inward-facing (or tissue-facing) side. The apertures 124 and 126 facilitate flow of fluids as suggested by arrows 128. The apertures 124 and 126 may take any shape, such as rectangular openings, circular openings, polygons, slits (elongated slots), etc. The non-adherent envelope 122 may be formed from a flexible film, such as a polyurethane film, a drape material, or any non-adherent material.

Reduced pressure may be applied by the reduced-pressure treatment subsystem 102 to the abdominal cavity 110 and the tissue site 106 to help promote removal of exudates, ascites, or other liquids, bacteria, fibrin, dead tissue, toxins, residual blood, etc. Reduced pressure may also be used in certain situations to stimulate growth of additional tissue. In the case of a wound at the tissue site 106, the growth of granulation tissue and removal of exudates and bacteria may help to promote healing of the wound. In the situation of a non-wounded or non-defective tissue, reduced pressure may be used to promote the growth of tissue that may be harvested and transplanted to another tissue site. In other situations, fluid removal may be the main reason for applying reduced pressure.

As used herein, "reduced pressure" generally refers to a pressure less than the ambient pressure at the tissue site 106. In most cases, the reduced pressure will be less than atmospheric pressure at which the patient is located. Alternatively, the reduced pressure may be less than the hydrostatic pressure of the tissue site 106. Unless otherwise indicated, values of pressure stated herein are gauge pressures.

The manifold 118 and the manifold member 120 are disposed in the abdominal cavity 110 and may be disposed at or near the tissue site 106. Typically, the non-adherent envelope 122, which contains the manifold member 120, is disposed against the tissue site 106 and, in particular, proximate the abdominal contents 116. The manifold 118 is disposed adjacent the non-adherent envelope 122. The manifold 118 and the manifold member 120 may take many forms. The term "manifold" as used herein generally refers to a substance or structure that is provided to assist in applying reduced pressure to, delivering fluids to, or removing fluids from a tissue site, such as the tissue site 106. The manifold 118 and the manifold member 120 typically include a plurality of flow channels or pathways that are interconnected to improve distribution of fluids provided to and removed from the area proximate the manifold 118 and the manifold member 120. The manifold 118 and the manifold member 120 may be formed from a biocompatible material that is capable of being placed in contact with tissue and that distributes reduced pressure. Examples of manifolds may include, without limitation, devices that have structural elements arranged to form flow channels, cellular foam, such as open-cell foam, porous tissue collections, and liquids, gels and foams that include or cure to include flow channels.

The manifold 118 and the manifold member 120 may be porous and may be made from foam, gauze, felted mat, or any other material suited to a particular biological application. In one embodiment, the manifold 118 and the manifold member 120 are made from a porous foam that includes a plurality of interconnected cells or pores that act as flow channels. The porous foam may be a polyurethane, open-cell, reticulated foam, such as a GranuFoam® material manufactured by Kinetic Concepts, Incorporated of San Antonio, Tex. Other embodiments may include "closed cells" at certain locations to help direct flow. In some situations, the manifold 118, the manifold member 120, and the non-adherent envelope 122 may be used to distribute fluids, such as medications, antibacterials, growth factors, and other solutions to the tissue site 106. Other layers may be included as part of the manifold 118 or the manifold member 120, such as absorptive material, wicking material, hydrophobic material, and hydrophilic material.

A sealing member 132 may be placed over the surface wound 111 in the epidermis 108 and, in particular, made to overlap the wound edges 112 to provide a pneumatic seal. Thus, the sealing member 132 provides a seal over the manifold 118 and the non-adherent envelope 122. The sealing member 132 may be a cover that is used to secure the manifold 118 and non-adherent envelope 122 at the tissue site 106. While the sealing member 132 may be impermeable or semipermeable, the sealing member 132 is capable of maintaining a reduced pressure at the tissue site 106 after installation of the sealing member 132 over the manifold 118. The sealing member 132 may be a flexible over-drape or film formed from a silicone based compound, acrylic, hydrogel or hydrogel-forming material, or any other biocompatible material that includes the impermeability or permeability characteristics desired for the intended tissue site.

The sealing member 132 may further include an attachment device 136 to secure the sealing member 132 to the patient's epidermis 108. The attachment device 136 may take many forms; for example, a sealing tape might be used or an adhesive 134 may be positioned along a perimeter of the sealing member 132 or any portion of the sealing member 132 to provide a pneumatic seal. The adhesive 134 might also be pre-applied and covered with a releasable member (not shown) that is removed at the time of application.

A first reduced-pressure interface 138, such as a port 140, or connector, may be used to deliver reduced pressure from a first reduced-pressure delivery conduit 142 to the manifold 118 to the reduced-pressure delivery conduit 142. The first reduced-pressure interface 138 may also deliver any exudate, ascites, or other fluids from the manifold 118 to the reduced-pressure delivery conduit 142. The reduced pressure in the manifold 118 pulls the fluid in the direction shown by arrows 144 and to the first reduced-pressure delivery conduit 142. The first reduced-pressure interface 138 permits the passage of fluid from the manifold 118 to the first reduced-pressure delivery conduit 142. For example, fluids collected from the tissue site 106 using the manifold member 120 may enter the first reduced-pressure delivery conduit 142 via the first reduced-pressure interface 138. In another embodiment, the reduced-pressure treatment subsystem 102 may exclude the first reduced-pressure interface 138, and the first reduced-pressure delivery conduit 142 may be inserted directly into the sealing member 132 and the manifold 118. The first reduced-pressure delivery conduit 142 may be a medical conduit, multi-lumen member, tubing, or any other means for delivering a reduced pressure.

A reduced-pressure subsystem 148 may be used to supply the reduced pressure that is delivered to the first reduced-pressure delivery conduit 142. The reduced-pressure subsystem 148 may include a first reduced-pressure unit, or source, 150 that delivers reduced pressure to a supply conduit 152, which delivers the reduced pressure to a three-way valve 154. One portion of the reduced pressure may leave the three-way valve 154 through a second reduced-pressure delivery conduit 156. Another portion of the reduced pressure may leave the three-way valve 154 through a reduced-pressure conduit 158. Located on the reduced-pressure conduit 158 may be any number of devices, such as a reduced-pressure feedback unit 160, which may, for example, give feedback to the three-way valve 154 concerning the regulation of the reduced pressure within the reduced-pressure conduit 158. The reduced-pressure conduit 158 delivers the reduced pressure to a canister 162, which is operable to hold any fluids delivered to the canister 162 from the tissue site 106. Reduced pressure leaving the canister 162 is delivered to the first reduced-pressure delivery conduit 142. The first reduced-pressure delivery conduit 142 may be referred to as delivering a second reduced pressure, or treatment reduced pressure. The second reduced pressure, or treatment reduced pressure, has been placed, by the reduced-pressure subsystem 148, at the desired pressure and conditions for use in reduced-pressure treatment at the tissue site 106.

A number of different devices, e.g., representative device 166, may be added to a medial portion 164 of the first reduced-pressure delivery conduit 142. The reduced pressure delivered to the first reduced-pressure delivery conduit 142 is typically selected to be in the range of −50 mm Hg to −500 mm Hg and more typically in the range −100 mm Hg to −300 mm Hg. The device 166 might be a pressure feedback device, a volume detection system, a blood detection system, an infection detection system, a flow monitoring system, a temperature monitoring system, etc. Some of these devices may be formed integrally with other parts; for example, the canister 162 may include one or more filters, e.g., a hydrophobic filter that prevents liquid from exiting.

There are many ways of developing the reduced pressure to be used with the reduced-pressure, wound-closure and treatment system 100. In the illustrative embodiment shown, the first reduced-pressure unit 150 is used for both applications, i.e., for wound closing and for reduced-pressure treatment. In an alternative embodiment, it may be desirable to use the first reduced-pressure unit 150 as the source for the second reduced-pressure delivery conduit 156 and have a second reduced-pressure unit 151 (shown in broken lines) to deliver reduced pressure to the reduced-pressure conduit 158.

As an aspect of the reduced-pressure, wound-closure and treatment system 100, it is also desirable to help provide a closing force to the surface wound 111 and, in particular, to apply a closing force between the wound edges 112. As shown in FIGS. 1 and 2, the wound-closure subsystem 104 may be used for this purpose. The wound-closure subsystem 104 develops a closing force represented by arrows 170. The closing force is communicated to the patient's epidermis 108 and urges the wound edges 112 towards each other. The wound-closure subsystem 104 may be a stand alone system for closing any surface wound or used as part of a larger system, e.g., the reduced-pressure, wound-closure and treatment system 100.

The wound-closure subsystem 104 may include a plurality of attachment members, e.g., a first attachment member 172 and a second attachments member 184, that are spaced around and proximate the wound edges 112 of the surface wound 111. The first attachment member 172 has a first base member 174 and a first wall member 176. The first base member 174 has a first side 178 and a second, inward-facing (patient-facing) side 180. The first base member 174 and first wall member 176 may be made from numerous materials, but a material is preferred that provides some flexibility; for example, the first attachment member 172 may be formed with the first base member 174 and the first wall member 176 made from polypropylene, or a rigid silicone, etc. A first adhesive 182 or other attachment device may be applied to the second, inward-facing (patient-facing) side 180 of first base member 174 to allow the first base member 174 to be releasably attached directly to a portion of the patient's epidermis 108 or indirectly if a polyurethane film or other sealing member 132 is placed on the epidermis 108 first. In addition to the adhesive 182, cement, staples, or sutures, or other invasive or non-invasive approaches might be used to attach the first base member 174 to intact epidermis tissue. The first attachment member 172 may be applied directly on top of the epidermis 108 or on top of the sealing member 132 so that whatever forces are applied on the first attachment member 172 are transmitted directly, or indirectly, to the epidermis 108. References to applying the attachment member 172 to the epidermis 108 should be deemed to include application on top of the sealing member 132.

Almost directly across the surface wound 111, e.g., epidermis wound, from the first attachment member 172 is the second attachment member 184. The second attachment member 184 is analogous to the first attachment member 172. While the wound-closure subsystem 104 only shows two attachment members 172, 184, other attachment members may be dispersed around the surface wound 111 in a spaced fashion. The two attachment members 172, 184 in conjunction with a sealed contracting member 188 allow the closing force, which is represented by arrows 170, to be developed, but additional attachment members allow forces to be developed radially across different shapes of the surface wound 111.

One or more of the attachment members, e.g., attachment member 172, has a reduced-pressure interface for receiving reduced pressure from the second reduced-pressure delivery conduit 156. For example, as shown clearly in FIG. 2, the first attachment member 172 may include a second reduced-pressure interface 183. The reduced pressure delivered through the second reduced-pressure interface 183 is used to develop the closing force.

The wound-closure subsystem 104 includes the sealed contracting member 188 to develop the closing force. The sealed contracting member 188 may be formed from a contracting manifold material, or member, which may be the same type of material as the manifold 118. Alternatively, it may be desirable to use a contracting manifold material that has fewer apertures or holes than the material used for the manifold 118 or a pneumatic device. In addition, it may be desirable to have a material that will contract less in the vertical (for the orientation shown in FIG. 1) and more in the horizontal, or lateral, plane (for the orientation shown in FIG. 1). The sealed contracting member 188 has a first side 190 and a second, inward-facing (patient-facing) side 192. The sealed contracting member 188 also has a peripheral edge 194. The sealed contracting member 188 may be sealed by having a first sealing member 196 (FIG. 2) applied to the first side 190 and a second sealing member 198 applied to the second, inward-facing side 192 of the sealed contracting member 188 and sealing the peripheral edges 194.

The peripheral edge 194 of the sealed contracting member 188 may be sealed by a peripheral sealing member 200. Alternatively or in addition, the first wall member 176 may also be used as the peripheral sealing member to seal the peripheral edge 194 or another piece of sealed material may be used. Similarly, the second, inward-facing side 192 may be sealed by placement against the sealing member 132 or the patient's epidermis 108. The sealed contracting member 188 may also be sealed by being coated with a gas-impervious material. The sealed contracting member 188 may be sealed with the first and second sealing members 196, 198, which may be formed from a polyurethane film or silicone. The first and second sealing members 196, 198 may be ultrasonically welded, or RF welded, or otherwise coupled at their ends to cover the peripheral edge 194. When reduced pressure is supplied to the sealed contracting member 188, the sealed contracting member 188 contracts to develop a closing force, which is represented by arrows 170.

The sealed contracting member 188 may be formed with an opening 201 on a portion of the sealed contracting member 188 for receiving an extension portion 202 of the first reduced-pressure interface 138. The extension portion 202 may extend through the sealed contracting member 188 and into the manifold 118. In an alternative embodiment, the second reduced-pressure interface 183 and the second reduced-pressure delivery conduit 156 may be omitted and a portion of the first reduced-pressure interface 138 fluidly coupled to the sealed contracting member 188. Thus, in this alternative embodiment, a single reduced-pressure source and conduit may be used for both providing a closing force and for the reduced-pressure treatment. The same is true of the illustrative embodiments of FIGS. 5A and 5B.

In operation, the reduced-pressure wound-closure and treatment system 100 may be used in a body cavity, e.g., the abdominal cavity 110, by first applying a manifold material on the abdominal contents 116. For example, the manifold member 120 with the non-adherent envelope 122 may be placed on the abdominal contents 116 and the manifold 118 disposed proximate the non-adherent envelope 122. The wound edges 112 of the surface wound 111 may be brought together to the extent possible, and then the sealing member 132 placed onto the epidermis 108 to provide a pneumatic seal over the surface wound 111. The first attachment member 172 may be applied using the first adhesive 182 to the patient's epidermis 108 (or on sealing member 132 as shown) proximate the wound edge 112. Similarly, the second attachment member 184 may be applied proximate the wound edge 112 on the opposite side. Either before the first and second attachment members 172 and 184 are applied to the epidermis 108, or afterwards, the sealed contracting member 188 is coupled to the first and second attachment members 172 and 184. This coupling may be accomplished in a number of different ways, such as by using adhesives 189 and 191, cements, bonding, etc. The first reduced-pressure interface 138, which may be the reduced-pressure port 140, may be applied such that an extension portion 202 reaches into the manifold 118. The first reduced-pressure delivery conduit 142 may be fluidly coupled to the first reduced-pressure interface 138 and fluidly coupled to the first reduced-pressure unit 150 (or an optional second reduced-pressure unit 151). The second reduced-pressure delivery conduit 156 may be fluidly coupled to the second reduced-pressure interface 183.

The reduced-pressure, wound-closure and treatment system 100 is activated such that the first reduced-pressure unit 150 delivers reduced pressure through the three-way valve 154, which prepares the second reduced pressure, or treatment reduced pressure, that is delivered to the first reduced-pressure delivery conduit 142 via the reduced-pressure conduit 158 and a first reduced pressure, or closing reduced pressure, that is delivered to the second reduced-pressure delivery conduit 156. The treatment reduced pressure delivered through the first reduced pressure delivery conduit 142 is realized at the manifold 118, which pulls fluids as suggested by arrows 144 and 128 and distributes reduced pressure within the abdominal cavity 110. At the same time, the closing reduced pressure is delivered through the second reduced-pressure delivery conduit 156 to the sealed contracting member 188, which causes the sealed contracting member 188 to contract developing a closing force, represented by arrows 170, which pulls the first and second attachment members 172 and 184 towards each other and thereby the wound edges 112.

Figure 3A:
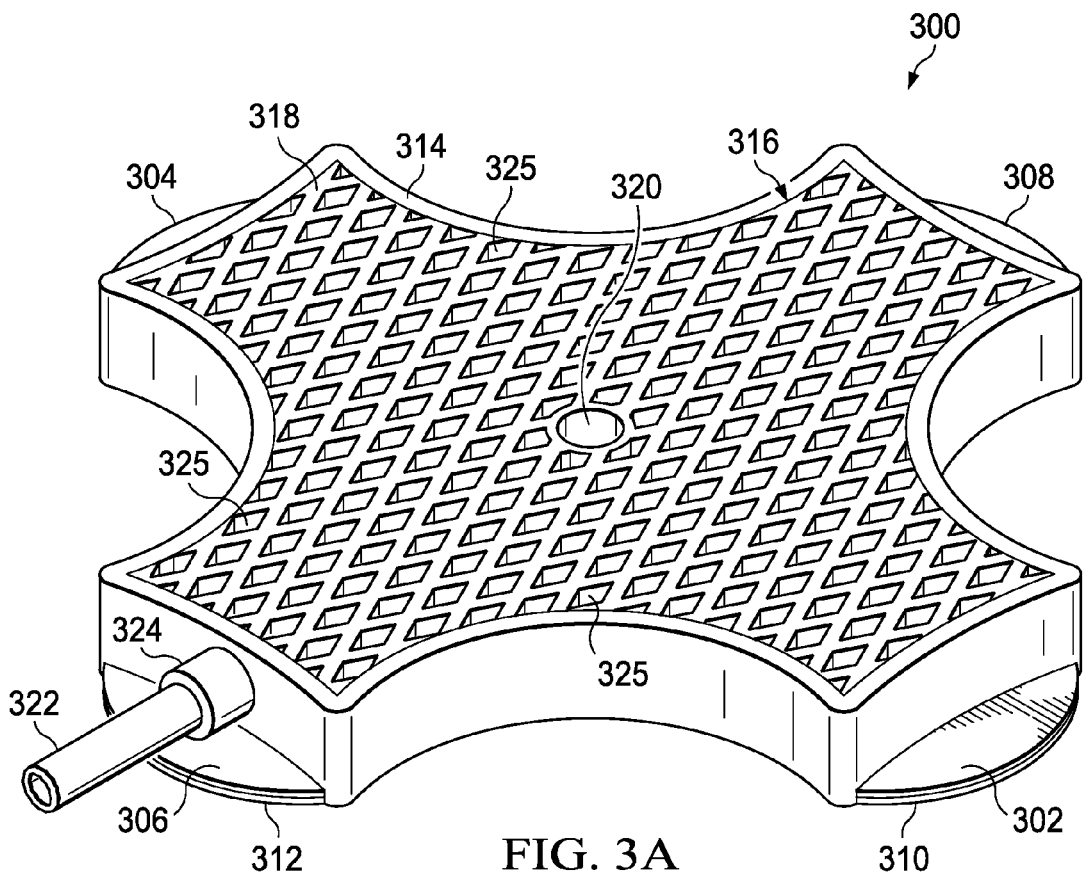
FIG. 3A is a schematic, perspective view of an illustrative embodiment of a portion of a reduced-pressure, wound-closure system.
Figures 3B, 3C:
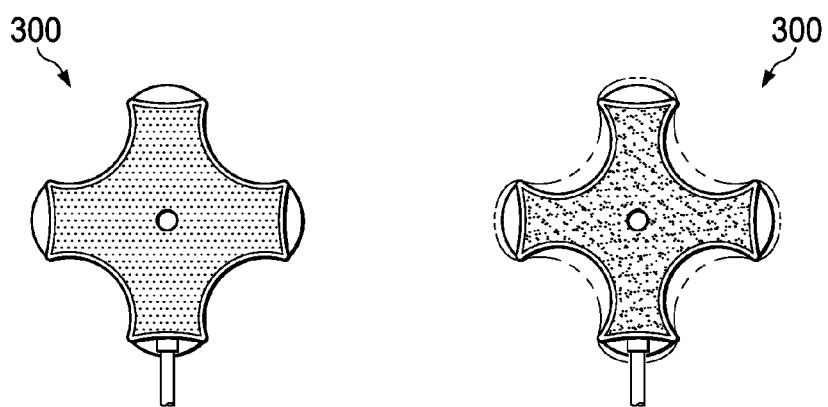
FIGS. 3B and 3C are schematic, plan views of the illustrative embodiment of FIG. 3A shown in a non-contracted position (FIG. 3B) and a contracted position (FIG. 3C)

Referring now to FIGS. 3A-3C, a reduced-pressure closure device 300 for providing a closing force on a surface wound is presented. The reduced-pressure closure device 300 may be used as part of a reduced-pressure, wound-closure and treatment system, like the reduced-pressure, wound-closure and treatment system 100 of FIG. 1 or as a stand alone device. The reduced-pressure closure device 300 has a plurality of attachment members: a first attachment member 302, a second attachment member 304, a third attachment member 306, and a fourth attachment member 308. Each attachment member 302, 304, 306, 308 has an attachment device for releasably attaching the attachment member to the patient's epidermis (or to a sealing member). For example, the first attachment member 302 includes an adhesive 310 for attaching the first attachment member 302 to the patient's epidermis and similarly, the third attachment member 306 has an adhesive 312. While not shown, the second and fourth attachment members also have a device, such as an adhesive, for securing the attachment members to a patient's epidermis. While non-invasive means are generally considered preferable, it may also be that the attachment members 302, 304, 306, and 308 may be secured using sutures, staples, or other invasive mechanical means. In addition, other non-invasive attachment devices may be used, such as cements, bonds, etc.

A wall 314, which is coupled to the plurality of attachment members, forms a circumferential wall having an interior space into which a contracting member 316, or contracting material, is placed. The sealed contracting member 316 is attached to the wall 314 at least at points proximate to each attachment member 302, 304, 306, 308. The wall 314 may be made of polypropylene, rigid silicone, or other semi-rigid material that allows the wall 314 to flex when the sealed contracting member 316 is contracted. The wall 314 may be molded, cast, or formed using other techniques. The sealed contracting member 316 may be made of the same kind of material as the sealed contracting member 188 in FIG. 1. The sealed contracting member 316 needs to be sealed and may be sealed by films, layers, or drapes. The film or other material on the sealed contracting member 316 may be applied to the first side, or a top side 318 (for the orientation shown). The sealed contracting member 316 may also be sealed, at least in part, with the wall 314 covering the peripheral edge, a sealing member (e.g., sealing member 132 in FIG. 1) providing a seal on the bottom, and a film or drape placed over the top side 318. A sealant may also be sprayed on to the top side 318 to form a seal. The sealed contracting member 316 may simply be enveloped in a polyurethane film that has been welded to form an envelope around the contracting member 316. An opening 320 may be formed through the sealed contracting member 316. The opening 320 allows for placement of part of a reduced-pressure interface that extends to a manifold, e.g., the manifold 118 in FIG. 1, below the reduced-pressure closure device 300. The opening 320 is analogous to opening 201 in FIG. 1 and is optional depending on desired use. A reduced-pressure conduit 322 delivers reduced pressure into the sealed contracting member 316. This may be accomplished by directly applying the reduced-pressure conduit 322 into any portion of the sealed contracting member 316, but may also be accomplished using a reduced-pressure interface 324, e.g., a port, formed on a portion of the wall 314.

In operation, the attachment members 302, 304, 306, and 308 are placed around the surface wound and releasably attached to the epidermis (or sealing member). Opposed attachment members, e.g., attachment members 302 and 304, are on opposite sides of the surface wound. Thus, for example, the first attachment member 302 and the fourth attachment member 308 may each be releasably secured to one side of a wound at different spaced portions and attachment members 304 and 306 may each be placed on opposite sides of the wound. As the reduced-pressure closure device 300 is installed, the reduced-pressure closure device 300 is initially in a non-contracted position. Once installed, reduced pressure is supplied to the reduced-pressure conduit 322 and the sealed contracting member 316 contracts causing at least portions of the outer wall 314 to be pulled towards one another and in turn to develop closing forces that are transmitted between attachment members, e.g., 302 and 304. Thus, the closing force is developed and transmitted to the epidermis through the attachment members 302, 304, 306, and 308. FIG. 3B shows the reduced-pressure closure device 300 in a non-contracted position, and FIG. 3C shows the reduced-pressure closure device 300 in the contracted position.

Figure 4A:
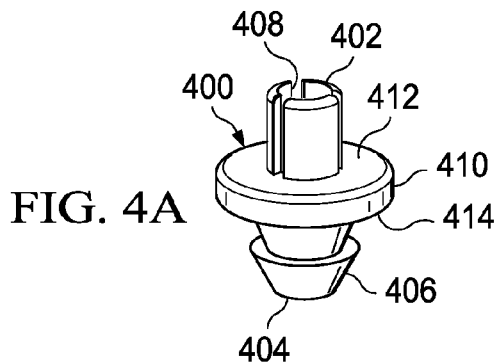
FIG. 4A is a schematic, perspective view of a reduced-pressure connector.
Figure 4B:
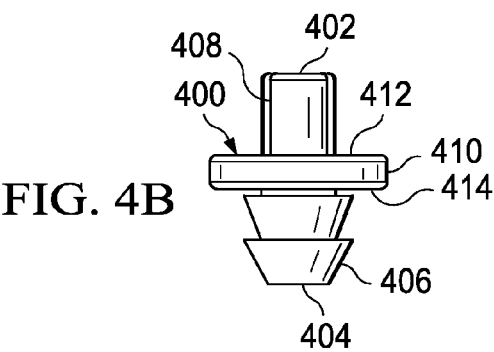
FIG. 4B is an elevational view of the reduced-pressure connector of FIG. 4A.

Referring now to FIGS. 4A and 4B, one illustrative embodiment of a reduced-pressure connector 400 is presented. The reduced-pressure connector 400 is operable to fluidly connect two different compartments or areas. In the illustrative embodiment of FIGS. 4A and 4B, the reduced-pressure connector 400 has a first end 402 and a second end 404. An entry portion 406 is formed on the second end 404. The entry portion 406 may be shaped as an inverted conical section to facilitate insertion through various materials, such as sealing members and manifolds. On the first end 402, a plurality of flutes 408 may be located to facilitate fluid flow. A flange portion 410 may be formed between the first end 402 and the second end 404. The flange portion 410 has a first surface 412 and a second surface 414. In an alternative embodiment, the first end 402 may also be shaped and configured for easy entry through a sealing member or other material. Two different, illustrative applications of the reduced-pressure connector 400 are shown in FIGS. 5A and 5B.

Figure 5A:
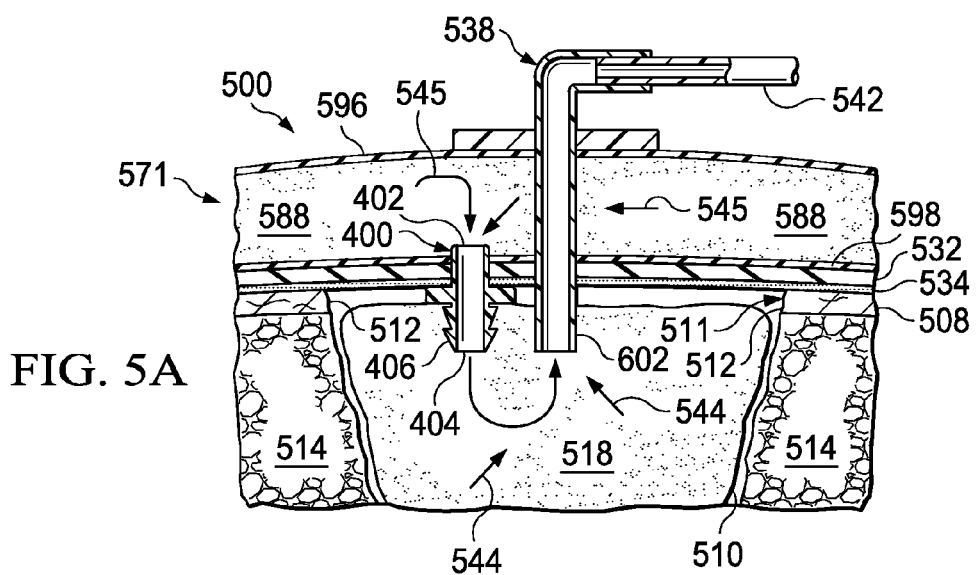
FIG. 5A is a schematic, cross-sectional view of a portion of another illustrative embodiment of a reduced-pressure, wound-closure and treatment system.
Figure 5B:
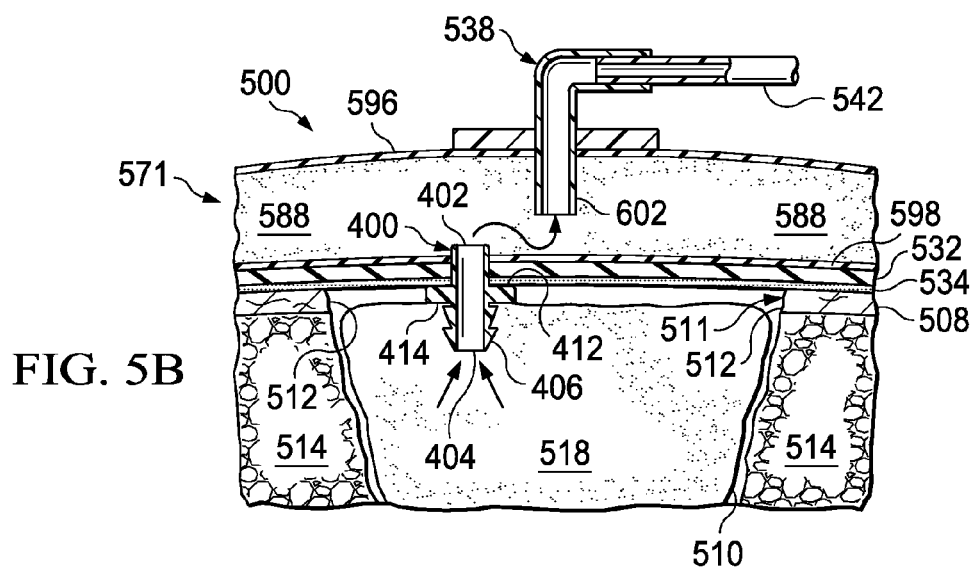
FIG. 5B is a schematic, cross-sectional view of a portion of another illustrative embodiment of a reduced-pressure, wound-closure and treatment system.

Referring to FIG. 5A, a portion of a reduced-pressure, wound-closure and treatment system 500 is presented. The reduced-pressure, wound-closure and treatment system 500 is analogous in most respects to the reduced-pressure, wound-closure and treatment system 100 of FIG. 1, and to indicate generally analogous parts, the reference numerals have been indexed by 400. A manifold 518 is placed within a body cavity, e.g., an abdominal cavity 510, to help provide reduced-pressure treatment therein. The manifold 518 is shown proximate to subdermal tissue 514 and a surface wound 511.

A sealing member 532 is placed on a patient's epidermis 508 over the abdominal cavity 510 and the surface wound 511. The surface wound 511 has wound edges 512. The sealing member 532 has an adhesive 534 helping to form a pneumatic seal with the patient's epidermis 508. The sealing member 532 as applied forms a pneumatic seal over the abdominal cavity 510.

A portion 571 of a wound closure device or subsystem is also presented. The portion 571 includes a portion of a sealed contracting member 588. The sealed contracting member 588 is sealed, at least in part, by a first sealing member 596 and a second sealing member 598. The sealed contracting member 588 is attached, at least at certain portions, to the patient's epidermis 508. When reduced pressure is supplied to an interior of the sealed contracting member 588, the sealed contracting member 588 contracts and thereby pulls inward and develops a closing force that is transmitted to the surface wound 511.

In the illustrative embodiments of FIGS. 5A and 5B, reduced pressure is supplied by a reduced-pressure source to a reduced-pressure conduit 542. The reduced-pressure conduit 542 is fluidly coupled to a reduced-pressure interface 538, which has an extension portion 602. In the embodiment of FIG. 5A, the extension portion 602 extends through the sealing member 532 and into the manifold 518. Thus, reduced pressure is delivered to the manifold 518 and pulls fluids towards the extension portion 602 as suggested by arrows 544. In this embodiment, the reduced-pressure connector 400 has been added. The reduced-pressure connector 400 is deployed with the first end 402 within the interior of the sealed contracting member 588 and the second end 404 within the manifold 518. The reduced-pressure connector 400 thereby fluidly couples the interior of the sealed contracting member 588 with the manifold 518. Reduced pressure is thereby delivered from the reduced-pressure interface 538, to the manifold 518, and to the interior of the sealed contracting member 588. The reduced pressure delivered through the reduced-pressure connector 400 pulls fluids within the sealed contracting member 588 as suggested by arrows 545.

The first surface 412 of the reduced-pressure connector 400 abuts the sealing member 532 and the second surface 414 abuts the manifold 518. The reduced-pressure connector 400 may be deployed in numerous ways. For example, with reference to FIGS. 3A and 5A, the reduced-pressure connector 400 can be placed over a cell, e.g., cell 325, of the sealed contracting member 316, and pushed through the sealing member thereon. The entry portion 406 is shaped to facilitate such an entry. The sealing member thereon should self-seal after insertion, but an additional portion of sealing material could also be added over the insertion point. During insertion, the reduced-pressure connector 400 is pushed into the sealed contracting member 316 until the second surface 414 abuts the second (bottom for orientation shown) sealing member 598 and the entry portion 406 extends out of the sealed contracting member 316. Referring to now primarily FIG. 5A, the entry portion 406 can then be inserted through the sealing member 532 and into the manifold 518. As noted earlier, numerous approaches may be taken for deploying the reduced-pressure connector 400 and the reduced-pressure connector 400 may take many different configurations, but the deployed reduced-pressure connector 400 functionally provides a fluid coupling of the sealed contracting member 588 and the manifold 518.

Referring now to FIG. 5B, another alternative is shown. In the embodiment of FIG. 5B, the extension portion 602 of the reduced-pressure interface 538 terminates within the sealed contracting member 588 and delivers reduced pressure within the sealed contracting member 588. The reduced-pressure connector 400 is deployed in the same manner as previously presented, but now delivers reduced pressure to the manifold 518. In other words, fluids are drawn through the manifold 518 through the reduced pressure connector 400 through an interior of the sealed contracting member 588 to the extension portion 602 of the reduced-pressure interface 538 and then through the reduced-pressure conduit 542.

Although the present invention and its advantages have been disclosed in the context of certain illustrative, non-limiting embodiments, it should be understood that various changes, substitutions, permutations, and alterations can be made without departing from the scope of the invention as defined by the appended claims.

We claim:

1. A reduced-pressure, wound-closure system for providing a closing force to a surface wound on a patient, the reduced-pressure, wound-closure system comprising:
   a plurality of attachment members for releasably attaching to the patient's epidermis proximate an edge of the surface wound, wherein each of the plurality of attachment members further comprises an attachment device;
   a circumferential wall coupled to the plurality of attachment members, the circumferential wall for disposing proximate the surface wound;
   a sealed contracting member coupled to at least a portion of the circumferential wall and configured to contract under reduced pressure to move the circumferential wall, the sealed contracting member pneumatically sealed from the surface wound;
   a reduced-pressure source fluidly coupled to the sealed contracting member and configured to deliver a reduced pressure to the sealed contracting member; and
   wherein the closing force is developed when the reduced pressure is supplied by the reduced-pressure source to the sealed contracting member.

2. The reduced-pressure, wound-closure system of claim 1 wherein the circumferential wall comprises polypropylene.

3. The reduced-pressure, wound-closure system of claim 1 wherein the circumferential wall comprises rigid silicone.

4. The reduced-pressure, wound-closure system of claim 1 wherein each attachment member of the plurality of attachment members comprises a first base member and the attachment device comprises adhesive.

5. The reduced-pressure, wound-closure system of claim 1 wherein the sealed contracting member comprises:
   a contracting manifold material having a first side and a second, inward-facing side, and a peripheral edge;
   a first sealing member disposed proximate the first side of the contracting manifold material;
   a second sealing member disposed proximate the second, inward-facing side of the contracting manifold material;
   a peripheral sealing member disposed proximate the peripheral edge of the contracting manifold material; and
   wherein the first sealing member, second sealing member, and peripheral sealing member are configured to pneumatically seal the contracting manifold material.

6. The reduced-pressure, wound-closure system of claim 5 wherein the peripheral sealing member comprises a third sealing member.

7. The reduced-pressure, wound-closure system of claim 5 wherein the peripheral scaling member comprises a wall.

8. The reduced-pressure, wound-closure system of claim 5 wherein each of the plurality of attachment members comprises:
- a first base member having a first side and a second, inward-facing side;
- a first wall coupled to the first base member; and
- wherein the attachment device comprises an adhesive that is coupled to the second, inward-facing side of the first base member.

9. The reduced-pressure, wound-closure system of claim 1, wherein each of the plurality of attachment members comprises a base coupled to the circumferential wall.

10. The reduced-pressure, wound-closure system of claim 1, wherein the attachment device comprises an adhesive.

11. The reduced-pressure, wound-closure system of claim 1, wherein the attachment device comprises a bond.

12. The reduced-pressure, wound-closure system of claim 1, wherein the attachment device comprises a suture.

13. The reduced-pressure, wound-closure system of claim 1, wherein the circumferential wall comprises a semi-rigid material configured to flex when the sealed contracting member is contracted.

14. A reduced-pressure, wound-closure system for providing a closing force to a surface wound on a patient, the reduced-pressure, wound-closure system comprising:
- a plurality of attachment members coupled to the patient's epidermis in a spaced relationship, wherein each of the plurality of attachment members comprises a base and an attachment device;
- a closed wall that defines an interior space;
- a sealed contracting member disposed within the interior space and coupled in at least two locations to the closed wall, the sealed contacting member pneumatically sealed from the surface wound and having a contracted position and a non-contracted position, wherein the closed wall is formed from a semi-rigid material that flexes when the sealed contracting member transitions from the non-contracted position to the contracted position; and
- a reduced-pressure interface coupled to the closed wall, wherein the reduced-pressure interface is fluidly coupled to the sealed contracting member for delivering reduced pressure to the sealed contracting member.

15. The reduced-pressure, wound-closure system of claim 14, further comprising a reduced-pressure subsystem for supplying reduced pressure, wherein the reduced-pressure subsystem is fluidly coupled to the reduced-pressure interface.

16. The reduced-pressure, wound-closure system of claim 14, having an aperture formed through the sealed contracting member.

* * * * *